United States Patent
Ory et al.

(10) Patent No.: US 6,443,964 B1
(45) Date of Patent: Sep. 3, 2002

(54) THREE-DIMENSIONAL OPEN-WORKED PROSTHETIC FABRIC

(75) Inventors: François Régis Ory, Fontaine Saint Martin; Michel Therin, Lyons; Alfredo Meneghin, Villefranche sur Saône, all of (FR)

(73) Assignee: Sofradim Production, Trevoux (FR)

( * ) Notice: Subject to any disclaimer, the term of this patent is extended or adjusted under 35 U.S.C. 154(b) by 0 days.

(21) Appl. No.: 09/463,318
(22) PCT Filed: Jul. 22, 1998
(86) PCT No.: PCT/FR98/01625
§ 371 (c)(1),
(2), (4) Date: Jan. 24, 2000
(87) PCT Pub. No.: WO99/05990
PCT Pub. Date: Feb. 11, 1999

(30) Foreign Application Priority Data

Aug. 1, 1997 (FR) .............................................. 97 10103

(51) Int. Cl.[7] .................................................. A61F 2/08
(52) U.S. Cl. .................. 606/151; 623/11.11; 623/14.13
(58) Field of Search ....................... 606/151; 623/14.13, 623/23.72, 23.74, 23.76, 11.11; 66/169 R

(56) References Cited

U.S. PATENT DOCUMENTS

| 3,124,136 A | | 3/1964 | Usher |
|---|---|---|---|
| 4,769,038 A | | 9/1988 | Bendavid et al. |
| 5,569,273 A | | 10/1996 | Titone et al. |
| 6,120,539 A | * | 9/2000 | Eldridge et al. .......... 623/14.13 |

FOREIGN PATENT DOCUMENTS

| EP | 0 621 014 A1 | 10/1994 |
|---|---|---|
| EP | 0 797 962 A1 | 10/1997 |

* cited by examiner

Primary Examiner—David O. Reip
Assistant Examiner—Julian W. Woo
(74) Attorney, Agent, or Firm—Oliff & Berridge, PLC

(57) ABSTRACT

An integral fabric made of at least one thread and having a thickness making apparent two opposite porous surfaces, the fabric having a honeycomb-like structure comprising transverse channels along the thickness of the fabric which are close and parallel to one another and emerging into an opening on either porous surface.

16 Claims, 3 Drawing Sheets

THREE-DIMENSIONAL OPEN-WORKED PROSTHETIC FABRIC

The present invention relates to a three-dimensional fabric, useful in particular in parietal and/or visceral surgery, but also able to be applied in other areas of surgery.

The present invention will be described more particularly with respect to a prosthetic fabric of said type, intended to be used for the repair of hernias or eventrations.

For a long time, surgeons have used flat prosthetic fabrics, that is to say two-dimensional, for repairing or replacing any part of the body, such as an aponeurosis, or a muscular wall, destroyed or damaged, for example as a result of a traumatism. Consequently, there are at present a very large number of such prosthetic fabrics, manufactured or obtained using various processes, for example weaving, knitting, or moulding, and which were designed often to carry out specific functions within the body in which they are implanted.

Such two-dimensional fabrics are for example described in the documents US-C-5 569 273 and 3 124 136.

However, such fabrics have several disadvantages, related to the very structure of the fabric, or to the choice of the base material used for making the threads, or again to the way in which the prosthetic fabric is manufactured. Thus, for example, the known prosthetic fabrics made of synthetic polymer material, are relatively inflexible.

It is also known that the tissual reaction to an implant is the result of a normal process of cicatrizing. Any tissual surgical traumatism is followed by a cascade of physiological events, the principal times of which are as follows:

t0: surgical traumatism, capillary breach;

t0 plus a few minutes: coagulation, fibrin network, release of chemotactic factors;

t0 plus 12 to 48 hours: polynuclear dominant leukocytic afflux;

t0 plus 4 to 8 days: fibroblast afflux t0 plus 24 hours to 5 days: macrophagic dominant leukocytic afflux;

t0 plus 8 to 21 days: connective differentiation of the cicatrizing reaction;

t0 plus 15 to 180 days: cicatrizing remodelling on contact with the implant.

Even if the exact mechanism are still unknown in certain cases, particularly with regard to the determinism of the intensity of the reaction, it therefore appears that the first 8 days are determinant since they condition the fibroblast afflux.

In non-bony tissue, the equilibrium of the reaction leads to the formation of a fibro-connective membrane which constitutes the interface between the implanted material and the surrounding healthy tissue. Whatever the type of implant, the zone directly affected by a conventional biocompatible material is a minimum of about 50 $\mu$m.

Furthermore, in the treatment of parietal inadequacies (principally hernias and eventrations), the prosthetic fabric has the task of providing additional mechanical strength to the surgical reconstruction, and it becomes more effective, and its local tolerance becomes better, as its tissue integration becomes more intimate and more advanced.

The Applicant has established, by its own research, whose results led to the present invention, that several parameters influence the tissual response to a prosthetic implant, namely:

the constituent material of the prosthesis and its possible products of degradation in a biological medium, which must not induce a toxic effect or an effect contrary to the sought effect. In the case of a prosthetic fabric implanted long-term, the aging of the material and its consequences (wear, ejection of components, etc.) are the most difficult factor to predict; only raw materials validated over a long period provide a maximum of safety;

as the organism, so to say, only sees the surface of the material, the properties of the latter assume significant importance. Among all of the surface parameters, the surface energy and the roughness have an important role. In effect, when it is sought to promote cellular adhesion, the surface must be hydrophilic (high surface energy) and smooth in comparison with a cell (of the order of one micron);

only the porosity accessible by the organism is useful with regard to the anchoring of the prosthetic fabric. This porosity in a given volume must be interconnected, and the interconnecting interstices must be sufficient for significant cellular penetration (of the order of 20 to 80 $\mu$m approximately), and for tissual differentiation (100 to 300 $\mu$m generally constitute a minimum for complete differentiation). It has been recalled above that the minimum distance for setting aside the tissual reaction from the direct influence of the prosthetic material is of the order of 50 $\mu$m, which means that for sizes of porosity less than 100 $\mu$m, the rehabilitation tissue will be entirely under the influence of the presence of the implant, with little possibility of completed tissual differentiation;

the vascularization and the biomechanical environment of the receiving site condition the intensity of the tissual response. A richly vascularized site (skin, muscles, etc . . . ) will react faster and more intensely than less vascularized tissues (rear chamber of the eye, bone, etc . . . ). Furthermore, the very nature of the receiving site conditions the capacity of regeneration to be identical to that of the wounded tissue. Bone, the connective tissues, mucous membranes, certain parenchymas (the liver for example) can regenerate identically with no significant fibrous scarring. On the other hand, other very specialized tissues (muscles, nerve tissues, etc . . . ) have lost all capacity to regenerate, the cicatrizing of these tissues therefore occurring only by fibrosis;

surgical traumatism constitutes one of the principal factors triggering the previously described cascade reaction. The bigger this is, the more intense the reaction will be and the more pronounced its consequences will be (cicatrizing delay, fibrous sequelae, pain, etc . . . ).

Considering the above, one of the objectives of a good prosthetic fabric is a tissual integration that is as fast as possible, procuring a mechanically satisfactory anchoring without extensive fibrosis, a source of discomfort and pain.

In order to try to achieve this objective, the Applicant has designed, manufactured and marketed, under the name "PAT" or "TET", a three-dimensional prosthetic fabric, comprising two opposite surfaces, porous or relatively rough, separated from each other by the thickness of the fabric, but linked to each other by binding threads, whose texture depends on the method of obtaining the fabric, for example by weaving and/or knitting.

One such three-dimensional fabric is for example described in the document EP-A-0 621 014, as the central part of a prosthetic assembly furthermore comprising edges formed from a single knitted layer.

In certain cases, the pattern of the prosthetic fabric determines, within its thickness, a plurality of transverse channels or cells substantially parallel to one another, emerging on either side of said fabric on the two porous surfaces respectively, in such a way that it is then possible to speak of an open-worked fabric, allowing direct progress of the repairing cells, starting from each of the surfaces of the fabric.

In the present application, certain terms have the following significance:

"fabric" refers to an assembly of threads, obtained in particular by knitting and/or by weaving;

"porous surface" refers to a surface of the fabric which exhibits numerous small orifices, or holes emerging in its surface, thereby conferring upon it a rough appearance.

This type of fabric has widely demonstrated its effectiveness, particularly in terms of the fastest possible integration in the receiving anatomical site, by procuring a mechanically satisfactory anchoring without extensive or significant fibrosis.

The present invention has however sought to improve the tissual integration of a three-dimensional prosthetic fabric such as previously defined, whilst lowering its intrinsic inflammatory power.

According to the present invention, the pattern of the fabric also determines, for each transverse channel or cell, an internal porous wall interconnecting with the adjacent channels.

Preferably, the passage interstices between channels have a width of between 100 and 300 µm.

The porosity of the channel wall is determined in particular by the fabric arrangement of the binding threads, which are themselves made from multifilaments of fibres (for example from polyester) having, by way of example, a diameter of between 10 and 15 µm.

Because of the invention as previously defined, the walls of the channels provide an anchoring zone for the fibrous reaction subject to the implant (the immediate environs of each thread), which nevertheless contributes to a relatively intimate and advanced tissual integration of the prosthetic fabric.

In effect, the Applicant has discovered that with a prosthetic fabric such as previously defined, the three-dimensional structure thus obtained improves cellular recolonization, whilst improving the integration of the fabric, because the available internal volume is increased. Furthermore, when the internal section of each cell or channel is substantially free of any binding thread, the inflammatory reaction of the prosthetic fabric in vivo is particularly reduced.

Furthermore, for an equivalent quantity of material per square metre, a three-dimensional structure such as defined previously makes it possible to open the interior of the fabric more widely than the exterior, which is favorable to a differentiation of a connective tissue histologically normal in the core of the implant. The multidirectional porosity according to the invention furthermore favors the drainage of the site and thus limits the risks associated with collections of liquids (seromas, hematomas, sepsis).

By virtue of the invention, the mechanical properties of the fabric are improved, without increasing the local density of prosthetic material, since the latter is distributed in volume in three directions.

Once the prosthetic fabric is implanted, the cells, present at the center of the volume created by the three-dimensional structure according to the invention, are at least 750 µm from any prosthetic material, if the dimensional conditions defined below are complied with. Thus, the colonizing cells are far from any influence able to delay or disturb the differentiation mechanisms, whilst being less than one millimeter from the receiving tissue, that is to say close to the elements providing the essential elements for a fast rehabilitation (progenitor base cells, blood capillaries, etc . . . ).

These conditions make it possible to obtain a mechanically satisfactory anchoring whilst preserving a thoroughly completed differentiation, such as encountered in a normal connective tissue.

In a preferred embodiment of the invention, each transverse channel emerges on at least one porous surface through an opening of hexagonal shape or through an opening shaped like a water drop. More preferentially, each transverse channel emerges on one porous surface through an opening of hexagonal shape, and on the other porous surface through an opening shaped like a water drop.

Preferentially, the mean diameter of the transverse channels is equal to or greater than 0.3 mm, preferably between 0.7 mm and 2 mm, and more preferably between 1.3 mm and 1.7 mm. In the same way, the transverse channels generally exhibit a length of between about 0.5 mm and 3 mm, and preferably between 1.6 mm and 2.1 mm, corresponding to the thickness of the fabric.

Preferably, the thickness of the fabric is at most equal to 3 mm, and more preferably between 1.7 mm and 2.5 mm.

The binding threads preferably each consist of a plurality of continuous filaments made of a biocompatible material, for example polyester. More preferably still, the fabric comprises two layers of knitted warp threads, determining on the outside the two porous surfaces, linked to each other, and preferably two layers of threads for intermediate binding.

In another preferred embodiment of the prosthetic fabric according to the invention, each transverse channel emerges on at least one porous surface through an opening of macropore type, whose diameter is between 0.7 mm and 2 mm, and more preferably between 1.3 mm and 1.7 mm.

Another subject of the present invention is a parietal and/or visceral prosthesis, obtained with a fabric such as defined previously.

Yet another subject of the present invention is the use of a fabric, according to the invention such as defined, in order to obtain a prosthetic product for surgical use, particularly for manufacturing a parietal and/or visceral prosthesis.

Preferably, the passage interstices between channels have a width of between 100 and 300 µm.

The present invention will be better understood with respect to the detailed description of some preferred embodiments of the invention, given by way of example, with reference to the accompanying figures, in which.

Figure 1:
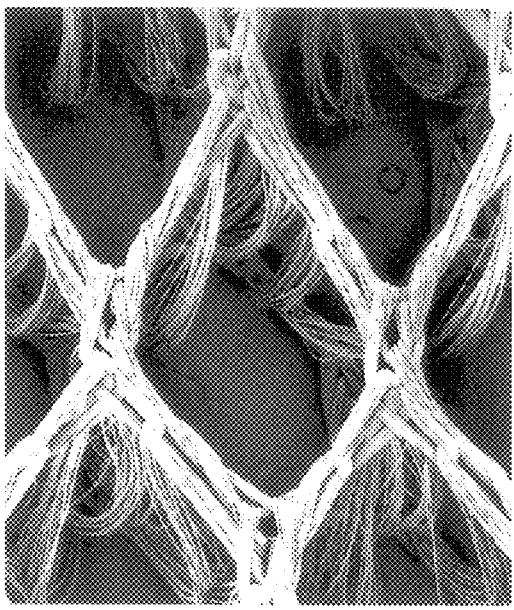
FIG. 1 is an image of one surface of a three-dimensional open-worked prosthetic fabric according to the invention, taken by electron scanning microscopy.
Figure 2:
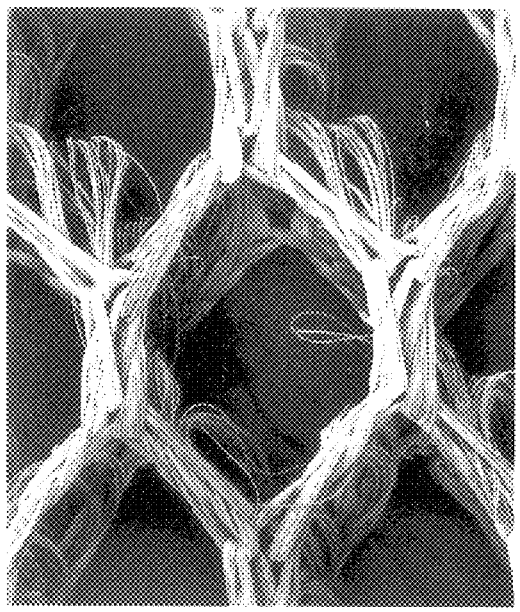
FIG. 2 is an image taken by electron scanning microscopy of the prosthetic fabric shown in FIG. 1, showing a view of the other surface.
Figure 3:
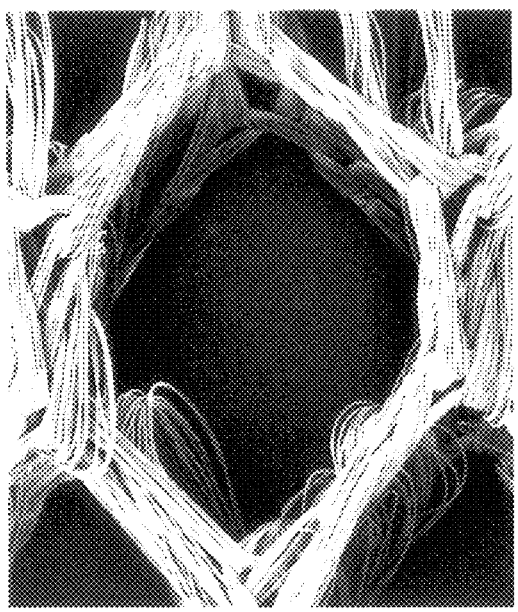
FIG. 3 is an image taken by electron scanning microscopy of the prosthetic fabric shown in FIG. 2, on a larger scale.
Figure 4:
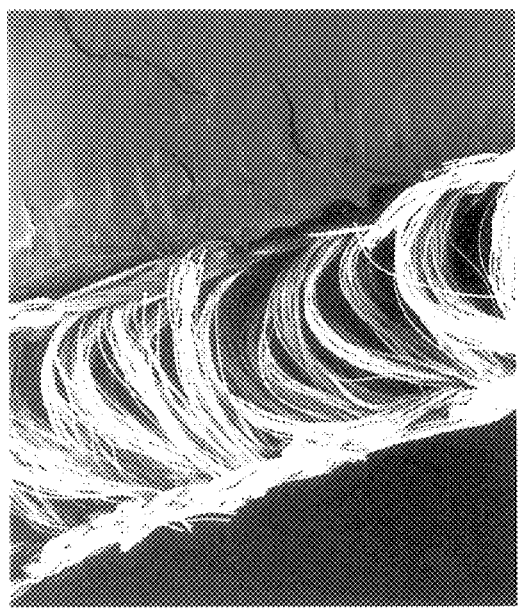
FIG. 4 is an image taken by electron scanning microscopy of the prosthetic fabric shown in FIGS. 1 to 3, in cross section or along its edge.

Referring to FIGS. 1 and 2, the three-dimensional open-worked prosthetic fabric according to a first preferred embodiment of the invention comprises two independent surfaces, one of them exhibiting openings shaped like water drops (see FIG. 1) and the other exhibiting openings of hexagonal shape (see FIG. 2). The openings of a same surface are defined by the peripheral edges, formed with the constituent threads of the prosthetic fabric, which is made of a synthetic or natural polymer material, resorbable or not, of the type currently used for such prosthetic fabrics, for example polypropylene, polyester or polyamide. In the described embodiment, a 50 decitex multifilament polyester is preferably used. As can be seen in FIGS. 1, 2 and 4, the layers of knitted warp threads determining the porous surfaces are connected to each other by two intermediate binding layers, which extend substantially perpendicularly from one surface toward the other surface, and which are distributed along the peripheral edges. The binding threads thus distributed form transverse channels, substantially parallel to each other, whose internal section is free of threads (see FIG. 3); these threads connect the openings of one surface to the openings of the other surface, which provides the prosthetic fabric with a honeycomb type structure. These transverse channels are substantially parallel to each other, emerging on either side of the fabric, on the two porous surfaces respectively.

According to the invention, the binding threads are disposed such that each transverse channel or cell has an internal porous lateral wall interconnecting with the adjacent channels, these interstices having a diameter of between 100 and 300 µm.

The transverse channels increase the speed of cellular colonization, once the fabric is implanted in vivo, because they facilitate the cellular afflux or routing to the site of the implantation. Furthermore, the virtual absence of threads in the very volume of the transverse channels makes it possible to lower the inflammatory reaction of the prosthetic fabric, which further favors a good implantation of the latter.

Figure 5:
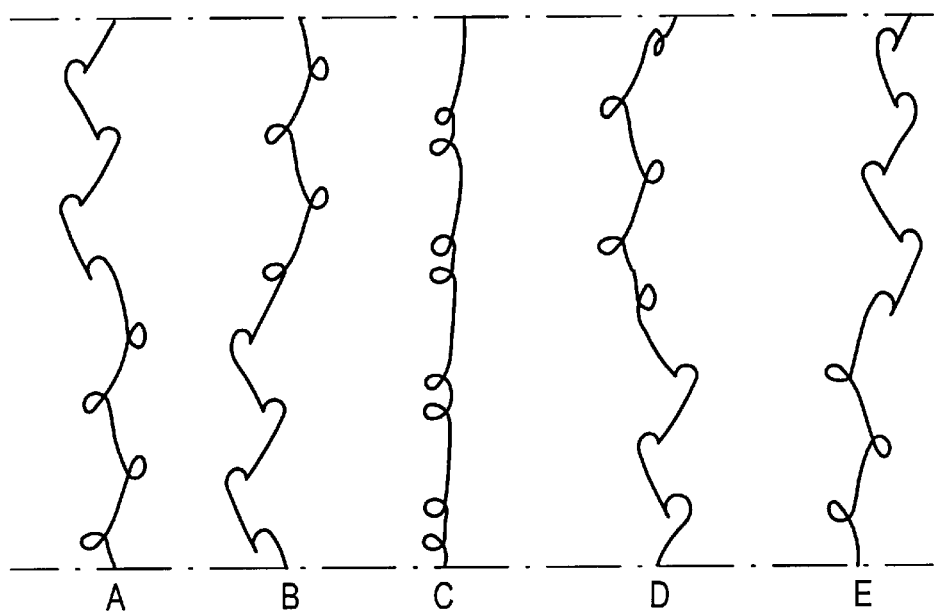
FIG. 5 is a diagrammatic drawing of the knitting pattern for obtaining a prosthetic fabric according to FIGS. 1 to 4.

Such a structure can be produced by warp knitting of five layers of threads, and in accordance with the diagrammatic drawing of FIG. 5. In this figure, each layer of threads is identified by a letter, ranging from A to E, the diagram in itself using a system of description of the knitting to be produced which is entirely customary and comprehensible for those skilled in the art, and which will not be described in greater detail here. According to FIG. 5, the preferred prosthetic fabric according to the present invention consist, as previously described, of two independent porous surfaces. These two surfaces, in the given example, themselves consist of two layers of threads, referenced A,B and D,E respectively, the layers A,B giving a surface with openings shaped like water drops, and the layers D,E giving a surface with hexagonal openings. The prosthetic fabric can be knitted on a double bed Rachel loom. In this case, all of the bars corresponding to the threads A,B and D,E are threaded one full-one empty. The layer of binding threads is represented by the reference C, and is threaded full. The different layers A–E of threads are all knitted at the same time. Thus the binding threads are distributed along the peripheral edges of the openings of each surface and extend substantially perpendicularly from one surface to the other surface, forming lateral interconnecting interstices with the other channels, whilst preventing binding threads from occupying too large a volume of the transverse channels which are formed. The final fabric can then be stabilized simply by passing it through an oven at a temperature of between about 170° C. and about 220° C. The thickness of the fabric obtained is of the order of 1.8 mm and of approximate weight 90 g/m². This fabric has a tensile strength, measured according to the NFG 07-119 standard, of between about 18 daN and 30 daN in warp and between about 9 daN and 15 daN in weft, for an elongation at break of about 25% to 37% in warp and about 60% to 88% in weft.

Figure 6:
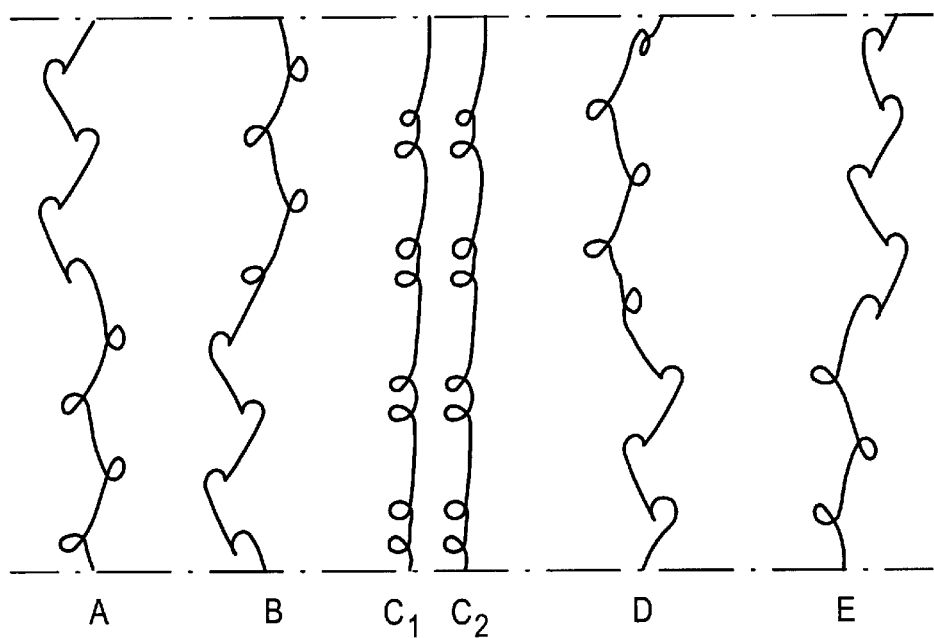
FIG. 6 is a diagrammatic drawing of the knitting pattern of a prosthetic fabric according to another preferred embodiment of the invention.

In another preferred embodiment of the present invention, both surfaces of the prosthetic fabric exhibit hexagonal openings. Such a fabric can be obtained by following the knitting diagram given in FIG. 6, wherein the four layers of threads A,B and D,E are again found, each pair constituting an independent porous surface, and connected to each other by two layers of binding threads C1,C2. In this embodiment, all of the bars, including those of the binding threads, are threaded one full-one empty.

What is claimed is:

1. A three-dimensional knit or weaved integral fabric made of at least one thread, having a thickness separating and making apparent two opposite porous surfaces, the two opposite porous surfaces defining a periphery region and an interior region interior to the periphery region, each having openings separated from one another, wherein the pattern of said fabric determines s a honeycomb-like structure comprising a multiplicity of transverse channels along the thickness of said fabric, substantially close and parallel to one another, emerging into one said opening on either porous surface with almost no distinct and parallel sheets or panels joined to one another, the multiplicity of transverse channels being defined at the periphery region and the interior region of the two opposite porous surfaces.

2. A fabric according to claim 1, wherein each said opening has an hexagonal shape.

3. A fabric according to claim 1, wherein each said opening has a water drop like shape.

4. A fabric according to claim 1, wherein each said opening of one porous surface has an hexagonal shape, and each said opening of the other porous surface has a water drop like shape.

5. A fabric according to claim 1, wherein said thread consists of a plurality of filaments or fibers of a biocompatible and/or resorbable material.

6. A fabric according to claim 5, wherein said biocompatible material is polyester.

7. A three-dimensional knit or weaved integral fabric made of at least one thread, having a thickness separating and making apparent two opposite porous surfaces, the two opposite porous surfaces defining a periphery region and an interior region interior to the periphery region, each having openings separated from one another, wherein the pattern of said fabric determines a multiplicity of transverse channels along the thickness of said fabric, substantially close and parallel to one another, emerging into one said opening on either porous surface, the multiplicity of transverse channels being defined at the periphery region and the interior region of the two opposite porous surfaces, said channels being separated from one another by internal porous wall internally interconnecting adjacent channels, said internal porous walls providing a multidirectional porosity throughout said fabric.

8. A fabric according to claim 7, wherein each said internal porous wall has interstices connecting said adjacent channels having a width of between 50 and 300 µm.

9. A three-dimensional knit or weaved integral fabric made of at least one thread having a thickness separating and making apparent two opposite porous surfaces, the two opposite porous surfaces defining a periphery region and an interior region interior to the periphery region, each having openings separated from one another, wherein the pattern of said fabric determines a honeycomb-like structure comprising a multiplicity of transverse channels along the thickness of said fabric, substantially close and parallel to one another, emerging into one said opening on either porous surface, the multiplicity of transverse channels being defined at the periphery region and the interior region of the two opposite porous surfaces, the internal section of each channel being substantially free of any crossing tread.

10. A three-dimensional knit or weaved integral fabric made of at least one thread, having a thickness separating and making apparent two opposite porous surfaces, the two opposite porous surfaces defining a periphery region and an interior region interior to the periphery region, each having openings separated from one another, wherein the pattern of said fabric determines a multiplicity of transverse channels along the thickness of said fabric, substantially close and parallel to one another emerging into one said opening on either porous surface, the multiplicity of transverse channels being defined at the periphery region and the interior region of the two opposite porous surfaces, said pattern being obtained by knitting two outside layers of warp threads in correspondence respectively to the two porous surfaces of the fabric, and at least one inside layer of thread for intermediately binding said outside layers.

11. A fabric according to claim 10, obtained by knitting on a double bed Rachel loom, all of the bars corresponding to the threads of the outside layers being threaded on full one empty, the inside layer being threaded full.

12. A prosthesis or implant for parietal and/or visceral surgery, comprising a fabric according to claim 10.

13. A three-dimensional knit or weaved integral fabric made of at least one thread, having a thickness separating and making apparent two opposite porous surfaces, each having openings separated from one another, wherein the pattern of said fabric determines a honeycomb-like structure comprising a multiplicity of transverse channels along the thickness of said fabric, substantially close and parallel to one another, emerging into one said opening on either porous surface with almost no distinct and parallel sheets or panels joined to one another, the multiplicity of transverse channels located substantially throughout the whole surface of the two opposite porous surfaces.

14. A three-dimensional knit or weaved integral fabric made of at least one thread, having a thickness separating and making apparent two opposite porous surfaces, each having openings separated from one another, wherein the pattern of said fabric determines a multiplicity of transverse channels along the thickness of said fabric, substantially close and parallel to one another, emerging into one said opening on either porous surface, the multiplicity of transverse channels located substantially throughout the whole surface of the two opposite porous surfaces, said channels being separated from one another by internal porous wall internally interconnecting adjacent channels, said internal porous walls providing a multidirectional porosity throughout said fabric.

15. A three-dimensional knit or weaved integral fabric made of at least one thread having a thickness separating and making apparent two opposite porous surfaces, each having openings separated from one another, wherein the pattern of said fabric determines a honeycomb-like structure comprising a multiplicity of transverse channels along the thickness of said fabric, substantially close and parallel to one another, emerging into one said opening on either porous surface, the multiplicity of transverse channels located substantially throughout the whole surface of the two opposite porous surfaces, the internal section of each channel being substantially free of any crossing thread.

16. A three-dimensional hit or weaved integral fabric made of at least one thread, having a thickness separating and making apparent two opposite porous surfaces each having openings separated from one another, wherein the pattern of said fabric determines a multiplicity of transverse channels along the thickness of said fabric, substantially close and parallel to one another, emerging into one said opening on either porous surface, the multiplicity of transverse channels located substantially throughout the whole surface of the two opposite porous surfaces, said pattern being obtained by knitting two outside layers of warp threads in correspondence respectively to the two porous surfaces of the fabric, and at least one inside layer of thread for intermediately binding said outside layers.

* * * * *